US010143598B2

(12) United States Patent
Strong et al.

(10) Patent No.: US 10,143,598 B2
(45) Date of Patent: Dec. 4, 2018

(54) METHOD FOR ASSEMBLING A WITHDRAWAL CORD WITH AN INTRAVAGINAL MEMBER

(71) Applicant: The Procter & Gamble Company, Cincinnati, OH (US)

(72) Inventors: Kevin Charles Strong, Loveland, OH (US); Evan Joseph Durling, West Chester, OH (US); Hinrich Knuth, Mason, OH (US); Enio Giovanni Cianci, S. Giovanni Teatino (IT)

(73) Assignee: The Procter & Gamble Company, Cincinnati, OH (US)

( * ) Notice: Subject to any disclaimer, the term of this patent is extended or adjusted under 35 U.S.C. 154(b) by 522 days.

(21) Appl. No.: 14/737,538

(22) Filed: Jun. 12, 2015

(65) Prior Publication Data
US 2015/0359684 A1    Dec. 17, 2015

Related U.S. Application Data

(60) Provisional application No. 62/011,079, filed on Jun. 12, 2014.

(51) Int. Cl.
| A61F 13/34 | (2006.01) |
| A61F 13/20 | (2006.01) |
| A61F 6/12 | (2006.01) |
| A61F 6/14 | (2006.01) |
| A61F 6/08 | (2006.01) |

(52) U.S. Cl.
CPC ............ *A61F 13/2085* (2013.01); *A61F 6/08* (2013.01); *A61F 6/12* (2013.01); *A61F 6/14* (2013.01); *A61F 13/208* (2013.01); *A61F 13/2082* (2013.01); *A61F 13/34* (2013.01)

(58) Field of Classification Search
CPC .............. A61F 13/2085; A61F 13/2088; A61F 13/2082; A61F 13/34; A61F 13/208; A61F 6/08; A61F 6/12; A61F 6/14; D04G 5/00
USPC .................. 28/120; 112/475.17; 600/135, 30; 604/385.18, 364; 128/839, 834, 840, 833
See application file for complete search history.

(56) References Cited

U.S. PATENT DOCUMENTS

| 3,946,463 | A |   | 3/1976 | Warnicke et al. | |
| 4,307,716 | A | * | 12/1981 | Davis | A61F 6/08 128/834 |
| 4,490,894 | A | * | 1/1985 | Friese | A61F 13/2085 28/120 |
| 4,775,377 | A |   | 10/1988 | Sweere | |
| 5,800,338 | A | * | 9/1998 | Kollerup | A61F 13/202 600/29 |

(Continued)

FOREIGN PATENT DOCUMENTS

GB          594580       11/1947

OTHER PUBLICATIONS

"Affix, v." dictionary.com. Web. Mar. 16, 2018.*
PCT International Search Report, dated Aug. 13, 2015, 42 pages.

*Primary Examiner* — Sally Haden
*Assistant Examiner* — Jillian K Pierorazio
(74) *Attorney, Agent, or Firm* — William E. Gallagher; Andres Ernesto Verlarde; Andrew J. Hagerty (57) ABSTRACT

The present invention relates to methods of assembling a withdrawal cord with an intravaginal member. In some embodiments, the withdrawal cord is affixed to an intravaginal member through the use of an anchor.

19 Claims, 8 Drawing Sheets

(56) References Cited

U.S. PATENT DOCUMENTS

| | | | |
|---|---|---|---|
| 7,011,033 B2* | 3/2006 | Sargent, Jr. | A61F 13/2085 |
| | | | 112/475.17 |
| 7,673,573 B2 | 3/2010 | Kondo et al. | |
| 7,677,189 B2 | 3/2010 | Kondo et al. | |
| 2003/0023214 A1* | 1/2003 | DiSalvo | A61F 13/2051 |
| | | | 604/364 |
| 2003/0225389 A1 | 12/2003 | Cassoni et al. | |
| 2014/0000629 A1* | 1/2014 | Durling | A61F 2/005 |
| | | | 128/840 |
| 2014/0100416 A1* | 4/2014 | Durling | A61F 2/005 |
| | | | 600/29 |
| 2014/0100417 A1* | 4/2014 | Durling | A61F 2/005 |
| | | | 600/30 |
| 2014/0115844 A1* | 5/2014 | Wolter | A61F 13/2065 |
| | | | 28/118 |

\* cited by examiner

METHOD FOR ASSEMBLING A WITHDRAWAL CORD WITH AN INTRAVAGINAL MEMBER

FIELD OF THE INVENTION

The present invention relates to methods of assembling a withdrawal cord with an intravaginal member. The intravaginal member can be, for example, a tampon or pessary body.

BACKGROUND OF THE INVENTION

Intravaginal devices such as tampons and pessaries generally employ a withdrawal cord to help users remove the devices after use. Typical withdrawal cords comprise flexible materials that are unwound from a supply. Most modern manufacturing lines operate at a fairly high throughput rate. And raw materials and components are often incorporated into such manufacturing lines in the machine direction. This can also be true for intravaginal device withdrawal cords. As sections of withdrawal cord are unwound and routed in the machine direction, a length of withdrawal cord needs to be accumulated and separated from the withdrawal cord supply for attachment to an intravaginal member. Accumulating the length of withdrawal cord while the intravaginal member to which it will be attached is moving at high rates in the machine direction can be difficult. Embodiments of the present invention address this challenge.

SUMMARY OF THE INVENTION

The present invention is directed to methods of assembling a withdrawal cord with an intravaginal member. In accordance with one embodiment, the method comprises the steps of: (a) providing an assembly surface comprising a seat; (b) providing a withdrawal cord supply; (c) disposing an intravaginal member onto and/or into the seat; (d) routing withdrawal cord from the withdrawal cord supply to a first position that is proximate the seat; (e) routing the withdrawal cord from the first position to a second position that is distal the seat; and (f) capturing the portion of the withdrawal cord that is located at the second position and affixing that portion to the intravaginal member.

In accordance with a second embodiment, the method comprises the steps of: (a) providing an assembly surface; (b) providing a withdrawal cord supply; (c) disposing an intravaginal member onto and/or into the assembly surface; (d) routing withdrawal cord from the withdrawal cord supply around a first translatable cord guide; (e) contacting a portion of the withdrawal cord with a second translatable cord guide; (f) moving the first translatable cord guide towards the intravaginal member; and (g) while conducting at least part of step (f) moving the second translatable cord guide towards the intravaginal member.

In accordance with a third embodiment, the method comprises the steps of: (a) providing an assembly surface; (b) providing a withdrawal cord supply; (c) disposing an intravaginal member onto and/or into the assembly surface; (d) routing withdrawal cord from the withdrawal cord supply around a pair of spaced apart cord guides; (e) capturing a portion of the withdrawal cord that bridges the pair of spaced apart cord guides with a withdrawal cord anchor; and (f) affixing the withdrawal cord anchor to the intravaginal member.

In accordance with a fourth embodiment, the method comprises the steps of: (a) providing an assembly surface that is moving in a first direction; (b) providing a withdrawal cord supply; (c) routing withdrawal cord from the withdrawal cord supply in the first direction; (d) disposing an intravaginal member onto and/or into the moving surface; (e) moving the withdrawal cord with a translatable cord guide in a second direction that is different from the first direction; (f) moving the withdrawal cord with the translatable guide in a third direction that is different from the first and second directions; and (g) affixing some of the withdrawal cord to the intravaginal member.

BRIEF DESCRIPTION OF THE DRAWINGS

The following detailed description of specific embodiments of the present invention can be best understood when read in conjunction with the drawings enclosed herewith.

The embodiments set forth in the drawings are illustrative in nature and not intended to be limiting of the invention defined by the claims. Moreover, individual features of the drawings and invention will be more fully apparent and understood in view of the detailed description.

DETAILED DESCRIPTION OF THE INVENTION

The following text sets forth a broad description of numerous different embodiments of the present invention. The description is to be construed as exemplary only and does not describe every possible embodiment since describing every possible embodiment would be impractical, if not impossible. And it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

It should also be understood that, unless a term is expressly defined in this specification using the sentence "As used herein, the term '________' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential to the present invention unless so stated. To the extent that any term recited in the claims at the end of this patent is referred to in this patent in a manner consistent with a single meaning, that is done for sake of clarity only so as to not confuse the reader, and it is not intended that such a claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

As used herein, the term "vaginal canal" refers to the internal genitalia of the human female in the pudendal region of the body. The terms "vaginal canal" or "within the vagina" as used herein are intended to refer to the space located between the introitus of the vagina (sometimes referred to as the sphincter of the vagina) and the cervix.

As used herein, the term "intravaginal device" means a device that is intended to be inserted at least partially within the vaginal canal and then removed via an affixed withdrawal cord. The intravaginal devices can be used to absorb menses and other bodily fluids (e.g., a tampon), deliver materials, and/or provide pressure or support (e.g., a pessary). The intravaginal devices generally include an intravaginal member or main body and a withdrawal cord affixed to the same. The intravaginal devices can optionally contain other features, such as, for example, an overwrap material. The intravaginal devices can be inserted into the vaginal canal digitally or via an applicator.

As used herein, the term "tampon" refers to any type of absorbent structure that can be inserted into the vaginal canal or other body cavity, such as, e.g., for the absorption of fluid, to aid in wound healing, and/or for the delivery of materials, such as moisture or active materials such as medicaments.

As used herein, the term "pessary" refers to any type of substantially non-absorbent (or low absorbent) structure for the purpose of reducing urine leakage and/or supporting a prolapsed uterus and/or bladder. Such pessaries can have any variety of shapes and sizes including cylinder, ovate, spherical, tubular, annual rings, "U" shaped, cup shaped, rings, cubes or donut shaped, and can function in any suitable manner, such as, e.g., by direct application of support, lever force, expansion of the device by selection of material, and/or by inflation of the device.

As used herein, the term "withdrawal cord" includes, but is not limited to, strings, ribbons, fibers, fabrics, cloths, and films. The withdrawal cord is preferably capable of being wound onto a core or other structure so that it can be unwound from the same on a manufacturing line for assembly with an intravaginal member.

As used herein, the term "affixed", "joined" or "attached" as used herein, encompasses configurations in which a first element is directly secured to a second element by affixing the first element directly to the second element, configurations in which the first element is indirectly secured to the second element by affixing the first element to intermediate member(s) which in turn are affixed to the second element, and configurations in which first element is integral with second element, i.e., first element is essentially part of the second element.

The present invention relates to methods for assembling a withdrawal cord with an intravaginal member. The methods generally are applicable to relatively high throughput, high speed processes and equipment, and the figures and accompanying figures illustrate exemplary embodiments of such. But the methods herein are also applicable to individual manufacturing processes and/or relatively slow processing speeds.

Figure 1:
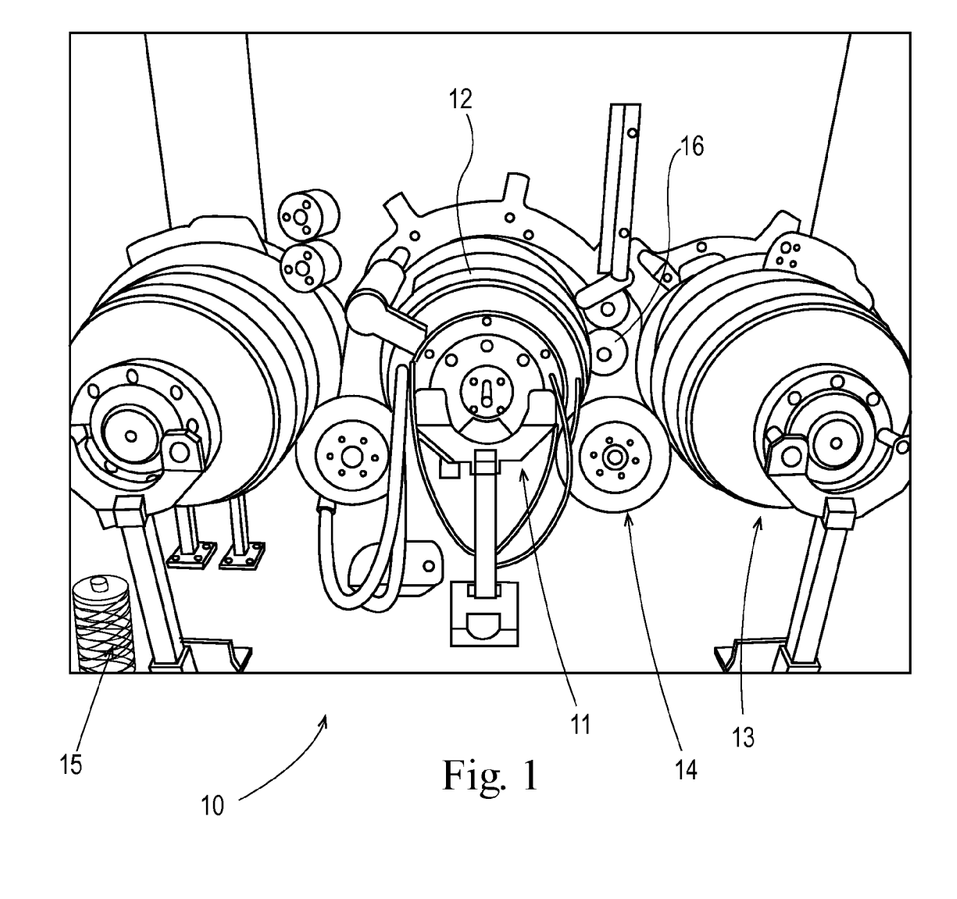
FIG. 1 is an elevation view of an exemplary apparatus that includes a withdrawal cord assembly module.

FIG. 1 includes an exemplary apparatus 10 that comprises a withdrawal cord assembly module 11, an intravaginal member feed module 13, a transfer roll 14 for transferring intravaginal members from feed module 13 to withdrawal cord assembly module 11, a withdrawal cord supply 15, and a transfer roll 16 for transferring a withdrawal cord anchor (shown and described below) from its supply to withdrawal cord assembly module 11. Withdrawal cord assembly module 11 comprises a rotary drum 12 to facilitate sufficient manufacturing throughput. Belts and other moveable surfaces can be used alternatively to a rotary drum. The skilled artisan will appreciate that apparatus 10 is only part of an overall manufacturing line that can include other components/manipulations towards creation of a final product.

Figure 2:
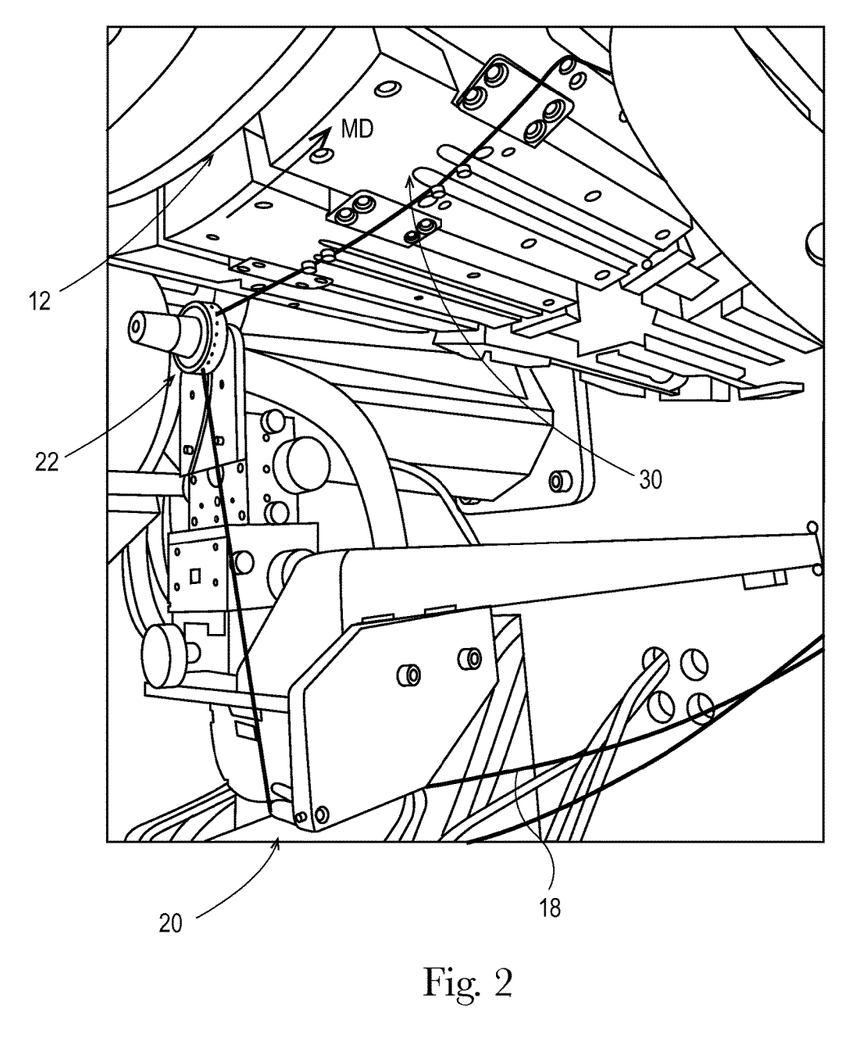
FIG. 2 is a partial bottom view of an exemplary withdrawal cord assembly surface.

Referring now to FIG. 2, a section of withdrawal cord 18 is unwound from the withdrawal cord supply and is routed underneath rotary drum 12, and through a pigtail guide 20 and tensioner 22 before reaching an assembly surface 30. At this point, the withdrawal cord 18 is moving in a machine direction MD along with the assembly surface 30.

Figure 3:
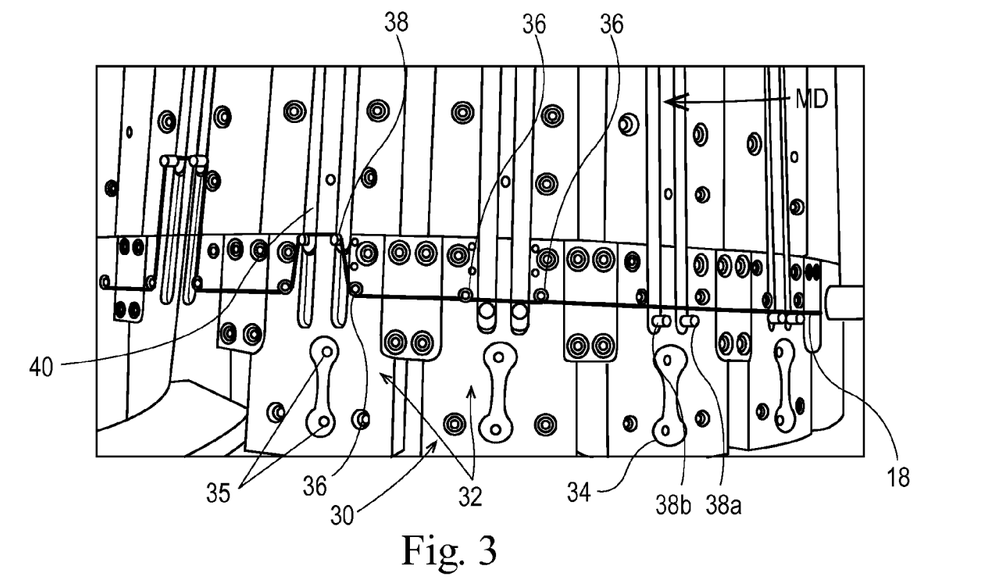
FIG. 3 is a partial plan view of an exemplary withdrawal cord assembly surface.

As shown in FIG. 3, assembly surface 30 includes a plurality of individual withdrawal cord assembly units 32, each of which comprises a seat 34 containing vacuum apertures 35 for receiving and temporarily holding an intravaginal member, a first pair of spaced apart cord guides 36 in the form of non-translatable roller guides, and a second pair of spaced apart cord guides 38 that are shown as translatable roller guides via moveable rods 40. The section of unwound withdrawal cord 18 is placed between cord guides 36 and cord guides 38. While the pair of spaced apart translatable cord guides 38 include individual guides 38a and 38b, a single cord guide having different elevations could also be employed. The machine direction MD in FIG. 3 is from left to right.

As drum 12 rotates, rods 40 are retracted which in turn moves translatable cord guides 38 from their first position that is proximate seat 34 to a second position that is distal seat 34. Cord guides 38 correspondingly move the section of withdrawal cord 18 away from the seat 34 in a direction that is different from the machine direction MD—for example, substantially orthogonal to the machine direction MD.

Figure 4:
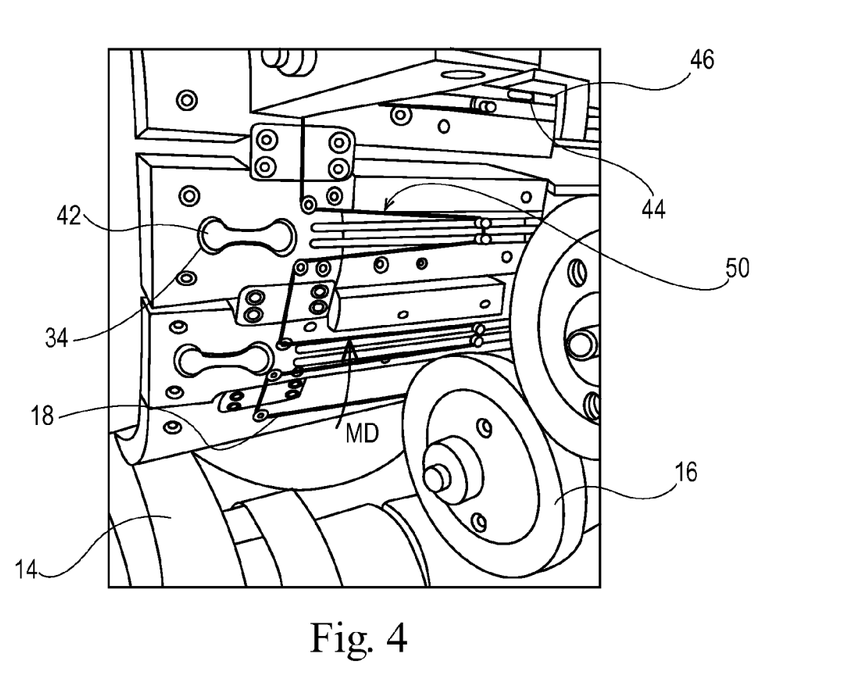
FIG. 4 is a partial side view of the withdrawal cord assembly surface shown in FIG. 3.

Referring now to FIG. 4, a withdrawal cord length 50 is created when the section of withdrawal cord 18 is moved away from seat 34. FIG. 4 also shows transfer roll 14 that transfers intravaginal members 42 from their supply to seats 34, and transfer roll 16 that transfers withdrawal cord anchors 44 from their supply to the end of a push rod core guide 46. The machine direction MD in FIG. 4 is from top to bottom.

Figure 5:
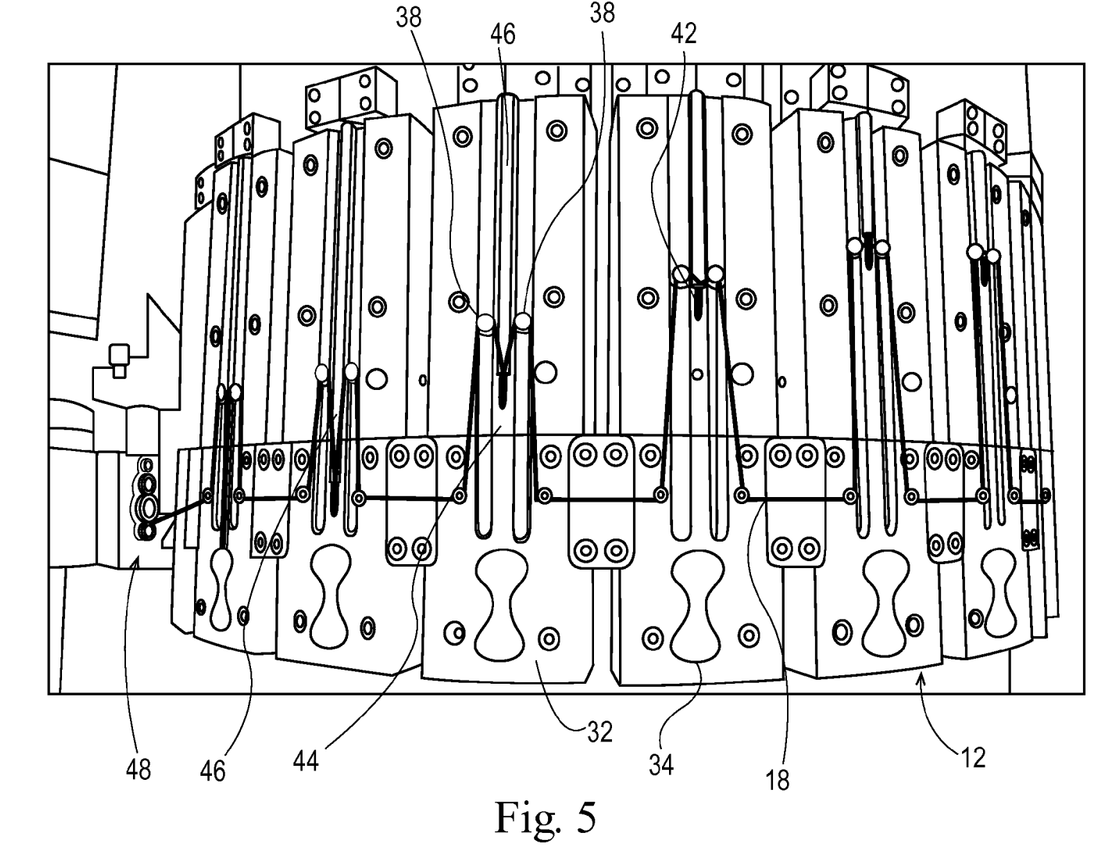
FIG. 5 is a plan view of the withdrawal cord assembly surface shown in FIGS. 3 and 4.
Figure 6:
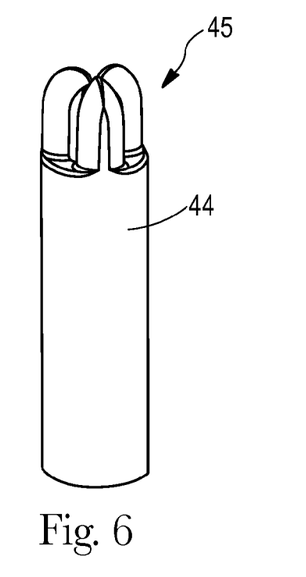
FIG. 6 is side view of an exemplary withdrawal cord anchor.

As shown in FIG. 5, when drum 12 rotates an additional amount, push rod 46 that includes an anchor 44 extends to contact a portion of the withdrawal cord 18 that bridges the pair of spaced apart cord guides 38. FIG. 6 illustrates an exemplary withdrawal cord anchor 44 that includes a plurality of flexible prongs 45 that enable anchor 44 to positively capture withdrawal cord 18.

Referring again to FIG. 5, after anchor 44 attaches to the withdrawal cord 18, push rod 46 continues to extend and move in a direction towards seat 34 that now contains an intravaginal member 42. Translatable core guides 38 also move in a direction back towards seat 34 (i.e., now a third direction of withdrawal cord movement). In one embodiment, and as shown in FIG. 5, push rod 46 moves at a different rate than cord guides 38.

Figure 7:
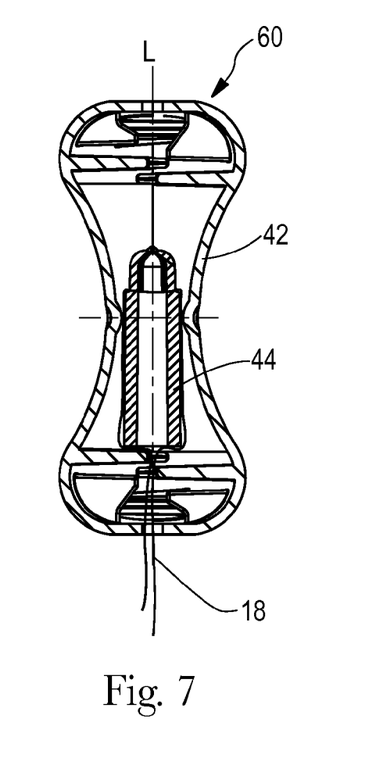
FIG. 7 is a cross-sectional view of an exemplary intravaginal device, illustrating the withdrawal cord anchor of FIG. 6 inserted into a hollow interior.

Push rod 46 extends further as drum 12 continues to rotate in the machine direction so that anchor 44, which is now attached to withdrawal cord 18, contacts an intravaginal member 42. In the embodiment shown in the figures, anchor 44 is inserted into the interior of the intravaginal member and is left within the interior when push rod 46 retracts. FIG. 7 is a cross-sectional view of an exemplary intravaginal device 60 comprising intravaginal member 42, withdrawal cord anchor 44, and part of withdrawal cord 18.

During or after anchor 44 is inserted into the interior of intravaginal member 42, at least a portion of the withdrawal cord length 50 is severed from the extended section of the withdrawal cord. As shown in FIG. 5, rotary drum 12 comprises an anvil 35 situated on either side of individual assembly units 32. A cutting assembly 48 mates with anvil 35 to sever the withdrawal cord 18. The resulting two free ends of the withdrawal cord extending from the intravaginal member can be joined to one another to create a loop that facilitates removal of an intravaginal device. Knotting is one technique for connecting the two free ends of the withdrawal cord.

One of ordinary skill in the art should appreciate that the figures and above description relate to one exemplary embodiment and that other embodiments are contemplated by the present invention. For example, while the process and intravaginal device shown and described above utilize an anchor for affixing a withdrawal cord to an intravaginal member, the withdrawal cord can be affixed without the use of an anchor via sewing, tying, adhesive application, or through a punch and loop technique, for example. In embodiments where an anchor is not employed, the push rod can contain a distal end that is configured for contacting the withdrawal cord and controllably moving the cord towards an intravaginal member.

The withdrawal cord material and configuration can vary. A fibrous string is an exemplary embodiment of the withdrawal cord. The string can comprise any suitable synthetic material. Suitable synthetic materials include, for example, non-natural material, such as, for example, polyethylene, polypropylene, polyethylene-polypropylene copolymer, polyvinyl alcohol, polyvinyl acetate, polyester, nylon, polylactides, polyhydroxylalkanoates, aliphatic ester polycondensates, cellulose acetate, and mixtures thereof. Such fibers can be formed in any suitable manner, such as, e.g., by melt spinning to produce staple fibers, monofilaments, multifilaments, continuous filaments, or other fibers useful in forming a withdrawal string. Fiber formation and processing generally includes the addition of finish compositions, such as, for example, lubricants and anti-statics.

The withdrawal string can be any suitable construction. For example, in certain embodiments, the withdrawal string can be a twisted or knitted construction containing multiple plies of yarn. The plies of yarn can be formed from twisted staple fibers or multiple continuous filaments. In addition, or alternatively, the weight or count of the yarn and/or the number of plies can be any weight or plies suitable for providing the desired strength, aesthetics, grippability, wearing comfort, handling, cost, and/or processing. In certain embodiments, the withdrawal string can be formed from 6 twisted plies of 10 count polypropylene yarn, one knitted ply of 10 count polypropylene yarns, or any other suitable construction The withdrawal string fibers can have any suitable cross-sectional shape, such as, e.g., round, tri-lobal, multi-lobal, delta, hollow, ribbon-shaped, and/or any other suitable shape, or mixtures thereof. Fibers with any suitable diameter can be used, such as, e.g., from about 0.5 to about 50 microns, such as, e.g., from about 1 to about 30 microns, such as, e.g., from about 10 to about 25 microns. Fiber diameter can be determined using any suitable means; however, for non-round fibers, diameter can typically be determined by reference to the diameter of a fiber with the same cross-sectional area as the non-round fiber.

As discussed above, one method of attaching a withdrawal cord to an intravaginal member is through the use of an anchor. An exemplary anchor is shown in FIG. 6. The anchor can be formed from polymeric materials, such as, for example, polycarbonate, polyester, polyethylene, polyacrylamide, polyformaldehyde, polymethylmethacrylate, polypropylene, polytetrafluoroethylene, polytrifluorochlorethylene, polyvinylchloride, polyurethane, nylon, silicone, or mixtures or blends thereof, or metallic materials. The anchor can be made my various methods including, for example, injection molding. The anchor can be any suitable shape. The anchor can be, for example, a disk, a cone, a star, a jack, a ball, a dumb bell, a drum, or a cross. The anchor can comprise one or more interconnected parts. The anchor can be a hook or multiple hooks. The anchor can have an insertion mode and a functional mode. The insertion mode can be the anchor in a non-expanded mode. The anchor can be compressible. The anchor can be flexible. The functional mode can be a volumetrically expanded mode. The anchor can transition between the insertion mode and the functional mode by hinge points in the anchor allowing the anchor to change volumetrically after it is affixed (for example inserted into an interior) to an intravaginal member.

The processes of the present invention are suitable for assembling a withdrawal cord with a number of different types of intravaginal products. Tampons and pessaries are two examples of such. Exemplary tampon embodiments will be described first.

Figure 8:
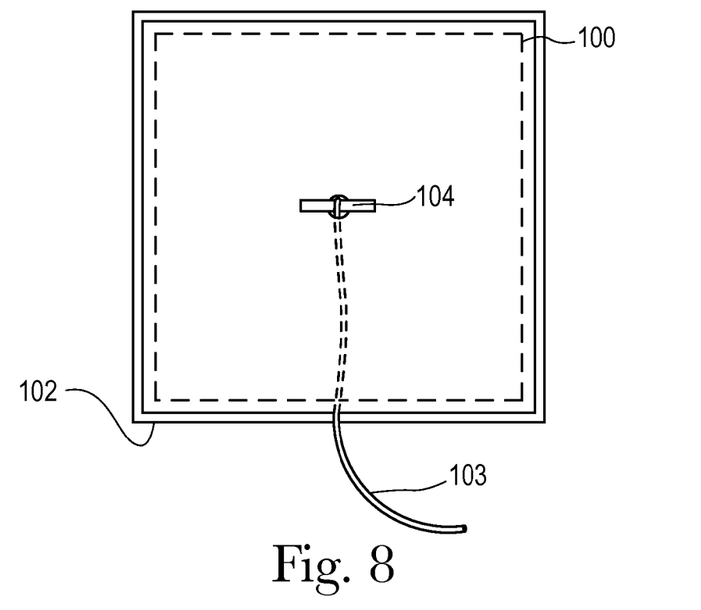
FIG. 8 is a side view of an exemplary tampon pledget.
Figure 9:
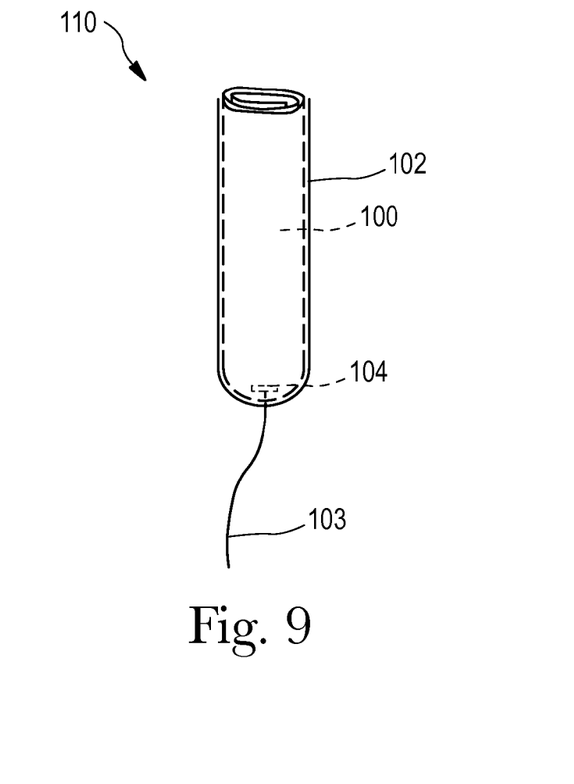
FIG. 9 is a side view of the tampon pledget of FIG. 8 after it has been manipulated into a final tampon form.

FIG. 8 shows a layer of absorbent material 100 that includes an optional overwrap material 102 and a withdrawal assembly including a withdrawal cord 103 and anchor 104. The layer of absorbent material 100 (or multiple layers of absorbent material) is manipulated to change its size/shape to the final tampon form to facilitate comfortable insertion into the vaginal canal. The size and/or geometry change with this manipulation can be accomplished numerous ways, including, for example, folding, rolling, pleating, compressing, and combinations thereof. FIG. 9 illustrates one exemplary embodiment of the components in FIG. 8 after the layer of absorbent material 100 has been compressed into a cylindrical tampon 110. As is apparent from FIG. 8, in some embodiments the withdrawal cord is affixed to the tampon absorbent material prior to manipulation to a final and different size/shape. In this embodiment, the layer of absorbent material 100 and optional overwrap material 102 would represent the intravaginal member in the process described in connection with FIGS. 1-7 above. A withdrawal cord can also be affixed to a tampon absorbent body after it has been manipulated in size and/or shape. Thus, a manipulated absorbent material can also represent the intravaginal member in the process described in connection with FIGS. 1-7.

The layer of absorbent material for constructing a tampon can include the following representative, non-limiting list: rayon (including tri-lobal and conventional rayon fibers), cotton, or comminuted wood pulp which is generally referred to as airfelt. Examples of other suitable absorbent materials include, but are not limited to, creped cellulose wadding; meltblown polymers including coform; chemically stiffened, modified, or cross-linked cellulosic fibers; synthetic fibers such as crimped polyester fibers; peat moss; foam; tissue including tissue wraps and tissue laminates; or any equivalent material or combinations of materials, or mixtures thereof.

Commercially available tampons generally comprise rayon, cotton, or combinations of both materials. These materials have a proven record of suitability for use in the human body. The rayon can be any suitable type typically used in disposable absorbent articles intended for in vivo use. Such acceptable types of rayon include GALAXY Rayon (a tri-lobed rayon structure) available as 6140 Rayon from Acordis Fibers Ltd., of Hollywall, England. SARILLE L rayon (a round fiber rayon), available from Acordis Fibers Ltd., is also suitable. Suitable cotton materials include, long fiber cotton, short fiber cotton, cotton linters, T-fiber cotton, card strips, and comber cotton.

Figure 10A:
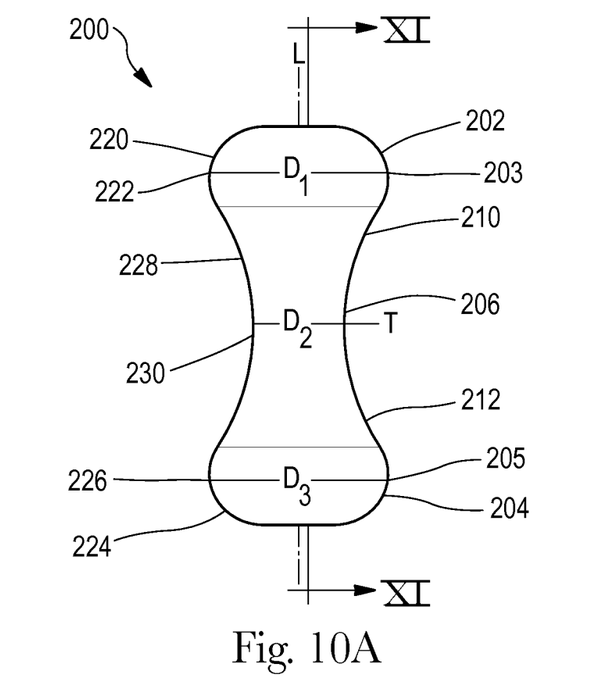
FIG. 10A is a side view of an exemplary pessary.
Figure 10B:
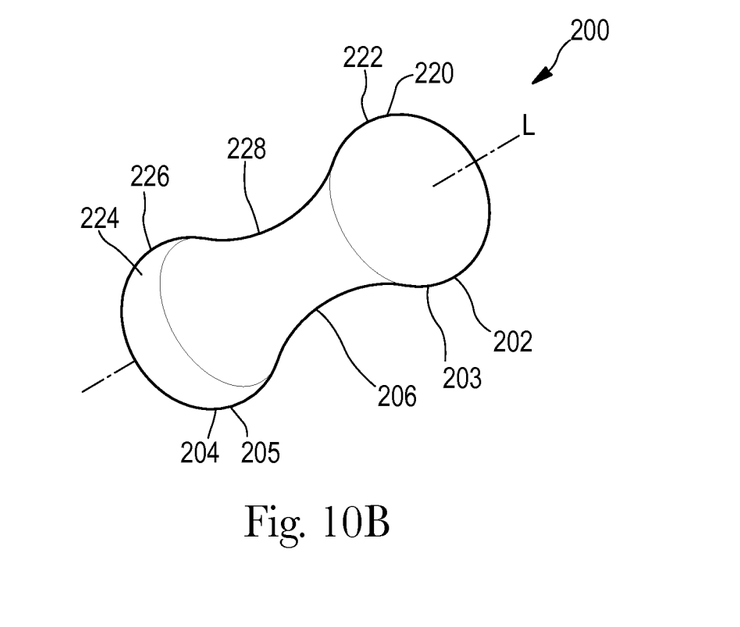
FIG. 10B is a perspective view of the pessary shown in FIG. 10A.

An exemplary pessary device 200 is shown in FIGS. 10A and 10B. The pessary device 200 includes an upper portion 202, a lower portion 204, a middle portion 206, a pressure region 203 of the upper portion 202, a pressure region 205 of the lower portion 204, a maximum diameter $D_1$, a minimum diameter $D_2$, a slope 210 extending from the upper portion 202 to the middle portion 206, a slope 212 from the middle portion 206 to the lower portion 204, a longitudinal axis (L) and a transverse axis (T). Pessary device 200 can have a top 220 that includes a convex portion 222, a base 224 that includes a convex portion 226, and sides 228 that include concave portions 230. The pessary device can be symmetric about the longitudinal axis, including for example, wherein the base is circular and symmetric about the longitudinal axis. The pessary device can include a third diameter $D_3$ that is greater than minimum diameter $D_2$, and convex portion 222 can be aligned with maximum diameter $D_1$ to provide pressure region 203, and convex portion 226 can be aligned with maximum diameter $D_3$ to provide pressure region 205.

Figure 11:
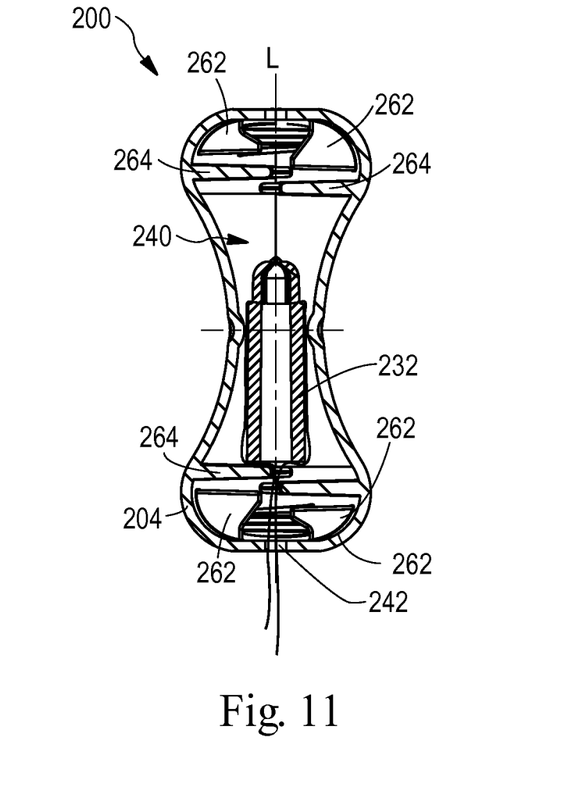
FIG. 11 is a cross-sectional view of the pessary of FIG. 10A taken through line XI-XI.

FIG. 11 shows a cross section of pessary device 200 taken along line XI-XI of FIG. 10A. Pessary device 200 includes a number of features that facilitate receipt and retention of withdrawal cord anchor 232. Pessary device 200 includes an interior region 240 that is hollow. Pessary device 200 can have an aperture 242 through any surface of the intravaginal device—aperture 242 is shown extending through lower portion 204 in FIG. 10. The interior region 240 of pessary device 200 can include one or more inwardly extending protuberances. As shown in FIG. 10, the hollow region 240 can have a first pair of protuberances 262 and a second pair of protuberances 264. The first pair of protuberances 262 can extend from an end of the pessary device towards the second pair of protuberances 264. The second pair of protuberances 264 can extend parallel the aperture at the end of the pessary device and be flexible. The second pair of protuberances 264 allow withdrawal cord anchor 232 to move past them when inserted through the aperture 242. Once the withdrawal cord anchor 232 has passed the second pair of protuberances 264, the first set of protuberances 262 prevent the second pair of protuberances 264 from bending towards aperture 242 thereby maintaining the withdrawal cord anchor 232 inside hollow region 240.

In some embodiments, the pessary device is non-expandable. A portion or region of the pessary device can flex or be deformed, such as, for example, in the region having the minimum diameter, but the pessary device does not expand and returns to the original configuration after deformation. As such, the pessary device does not include any mechanical or other means that requires the user to change the size or shape of the pessary device during use, such as, for example, before or after insertion or prior to withdrawal. This provides for a pessary device that has a size upon withdrawal that is the same as the size during use, which can provide for improved comfort during use and withdrawal.

The pessary device can be a unitary construction. For example, the pessary device can include a continuous outer shell that defines the entire exterior surface of the pessary device. The outer shell can be smooth or textured. The outer shell can be permeable to fluid, such as, for example, by the inclusion of holes, pores, or other suitable openings. Alternatively, the outer shell can be impermeable to fluid such that fluid cannot enter the device. In addition, the pessary device can include an opening in the top and/or base. The pessary device can include an opening in the top and/or base and the outer shell is not permeable to fluid such that fluid cannot enter the device except through the opening in the top and/or base. The opening in the top and/or base to the hollow interior may have engaging members. The engaging members may be triangles, half circles, quarter circles, and/or geometric shapes with points. Engaging members are further described in U.S. Patent Publication No. 2014/0000628 A1, filed Jun. 29, 2012.

The pessary device can be constructed from two or more pieces. The two or more pieces can snap fit together to form a continuous outer shell that defines the entire exterior surface of the pessary device. In addition, the pessary device can include an aperture in the top and/or base.

The pessary device can have a hollow interior. The pessary device can have an outer periphery defining a total area of the device and an inner periphery defining an open area of the device. The open area can be any suitable size, such as, for example, between about 5% to about 95% of the total area, such as, for example, from about 10% to about 90% of the total area, from about 15% to about 85% of the total area, or from about 20% to about 80% of the total area. In addition, the pessary device also can have a wall thickness that is suitable to maintain the pessary configuration. The wall thickness can be greater than about 1 mm, such as for example, about 2 mm, about 3 mm, about 4 mm, about 5 mm, or greater. The wall thickness can be constant or varied along the length of the pessary device and/or around the circumference of the pessary device.

Pessary devices can be fabricated using any suitable materials and methods. For example, pessaries can be formed from polymeric materials, such as, for example, polycarbonate, polyester, polyethylene, polyacrylamide, polyformaldehyde, polymethylmethacrylate, polypropylene, polytetrafluoroethylene, polytrifluorochlorethylene, polyvinylchloride, polyurethane, nylon, silicone, or mixtures or blends thereof, or metallic materials. In certain embodiments, the pessary devices are not formed from absorbent material such as, for example, fibrous material or absorbent foam.

Pessary devices can be formed in any suitable manner, such as, for example, using injection molding, blowmolding, or other suitable methods of forming the pessary device. Pessary devices can be assembled by snap fitting two or more pieces together.

The tampon absorbent bodies and pessary bodies can include an optional overwrap material. In tampon embodiments, the optional overwrap material is liquid permeable via natural liquid pathways or aperturing. In pessary embodiments, the optional material can be liquid permeable or liquid impermeable. Exemplary overwrap materials include non-wovens comprising a blend of synthetic and natural fibers, and polymeric films. The synthetic fibers may include, but are not limited to, fibers such as polyester, polyolefin, nylon, polypropylene, polyethylene, polyacrylic, cellulose acetate, or bicomponent fibers. Natural fibers may include, but are not limited to, those commonly known to be non-synthetic and of natural origin such as cotton and/or rayon. Polymeric films can comprise polyolefins and polyesters, for example. Depending on their intended use, the polymeric films may be made liquid permeable through aperturing or other "opening" technique.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of assembling a withdrawal cord with a pessary device, the method comprising the steps of (a) providing an assembly surface comprising a seat; (b) providing a withdrawal cord supply; (c) disposing a pessary onto and/or into the seat; (d) routing a section of withdrawal cord from the withdrawal cord supply to a first position that is proximate the seat; (e) routing the section of withdrawal cord from the first position to a second position that is distal the seat; (f) capturing a portion of the section of withdrawal cord at the second position on a withdrawal cord anchor; and (g) inserting the withdrawal cord anchor with a portion of the section of the withdrawal cord into the pessary device, whereby the withdrawal cord anchor and the portion of the section of the withdrawal cord remain inside the pessary device following completion of assembly.

2. The method of claim 1, wherein the assembly surface is associated with a rotating member.

3. The method of claim 1, wherein step (e) is accomplished with a translatable cord guide.

4. The method of claim 1, wherein step (e) is accomplished with a pair of translatable cord guides.

5. The method of claim 3, wherein the translatable cord guide is in communication with a a reciprocating member.

6. The method of claim 1, wherein step (d) is accomplished via a non-translatable guide.

7. The method of claim 1, wherein the withdrawal cord anchor is temporarily in communication with a reciprocating member.

8. The method of claim 1, further comprising the step of (h) routing the section of withdrawal cord from the second position to a third position that is proximate the seat.

9. The method of claim 8, wherein step (h) is accomplished via a second non-translatable guide.

10. A method of assembling a withdrawal cord with a pessary device, the method comprising the steps of:
    (a) providing an assembly surface;
    (b) providing a withdrawal cord supply;
    (c) disposing a pessary device onto and/or into the assembly surface;
    (d) routing a section of withdrawal cord from the withdrawal cord supply around a first translatable cord guide;
    (e) contacting the section of the withdrawal cord with a second translatable cord guide;
    (f) moving the first translatable cord guide towards the pessary device; and
    (g) while conducting at least part of step (f) moving the second translatable cord guide towards the pessary device,
       wherein the second translatable guide comprises a withdrawal cord anchor and wherein the withdrawal cord anchor is inserted into the pessary device and is left inserted in the pessary device following completion of assembly.

11. The method of claim 10, wherein the first translatable guide is a roller guide in communication with a reciprocating member.

12. The method of claim 10, wherein the first translatable cord guide comprises two spaced apart cord guides, and wherein the second translatable cord guide can travel between the two spaced apart cord guides.

13. The method of claim 10, wherein the second translatable guide translates via a push rod.

14. The method of claim 10, wherein the first translatable cord guide is moved at a different rate in step (f) than the second translatable cord guide in step (g).

15. A method of assembling a withdrawal cord with a pessary device, the method comprising the steps of:
    (a) providing an assembly surface;
    (b) providing a withdrawal cord supply;
    (c) disposing a pessary device onto and/or into the assembly surface;
    (d) routing a section of withdrawal cord from the withdrawal cord supply around a pair of spaced apart cord guides;
    (e) capturing the section of withdrawal cord with a withdrawal cord anchor; and
    (f) affixing the withdrawal cord anchor to the pessary device,
wherein the withdrawal cord anchor is inserted into the pessary device and is left inside the pessary device following completion of assembly.

16. The method of claim 15, wherein each of the pair of spaced apart cord guides comprises a roller guide in communication with a reciprocating member.

17. The method of claim 15, wherein the withdrawal cord anchor is temporarily disposed in communication with a reciprocating member.

18. The method of claim 15, wherein step (f) comprises inserting the withdrawal cord anchor into a hollow interior of the pessary device.

19. A method of assembling a withdrawal cord with a pessary device, the method comprising the steps of:
(a) providing an assembly surface that is moving in a first direction;
(b) providing a withdrawal cord supply;
(c) routing a section of withdrawal cord from the withdrawal cord supply in the first direction;
(d) disposing a pessary device onto and/or into the moving surface;
(e) moving the section of withdrawal cord with a translatable cord guide in a second direction that is different from the first direction;
(f) moving the section of withdrawal cord with the translatable guide in a third direction that is different from the first and second directions; and
(g) affixing a portion of the section of withdrawal cord to the pessary device, wherein step (e) is accomplished via a withdrawal cord anchor that is temporarily disposed in communication with a reciprocating member and wherein the withdrawal cord anchor is inserted into a hollow interior of the pessary device and is left within the interior following completion of assembly.

* * * * *